United States Patent [19]
Picard et al.

[11] Patent Number: 6,117,869
[45] Date of Patent: Sep. 12, 2000

[54] COMPOUNDS FOR AND METHODS OF INHIBITING MATRIX METALLOPROTEINASES

[75] Inventors: Joseph Armand Picard, Canton; Bruce David Roth, Plymouth; Drago Robert Sliskovic, Saline, all of Mich.

[73] Assignee: Warner-Lambert Company, Morris Plains, N.J.

[21] Appl. No.: 09/361,077

[22] Filed: Jul. 26, 1999

Related U.S. Application Data

[60] Provisional application No. 60/095,338, Aug. 4, 1998.

[51] Int. Cl.$^7$ .................... C07D 327/08; C07D 339/08; C07D 311/82; A61K 31/39; A61K 31/385

[52] U.S. Cl. ................ 514/227.5; 549/16; 549/17; 549/359; 549/392; 549/27; 544/347; 544/348; 544/58.1; 544/104; 546/103; 548/504; 548/335.1; 514/297; 514/227.8; 514/227.5; 514/229.8; 514/415; 514/396; 514/434; 514/452; 514/454; 514/437; 514/255.05; 514/255.06; 562/427

[58] Field of Search ................. 549/16, 17, 359, 549/392; 514/434, 437, 452, 454, 562; 562/427

[56] References Cited

U.S. PATENT DOCUMENTS 4,066,773  1/1978  Okamoto et al. .............. 424/267

FOREIGN PATENT DOCUMENTS 0307879  3/1989  European Pat. Off. .
9700675  1/1997  WIPO .

OTHER PUBLICATIONS

Sato H., et al., "A matrix metalloproteinase expressed on the surface of invasive tumour cells", *Nature*, vol. 370, 1994, pp 61–65.

Galis Z. S., et al., "Increased expression of matrix metalloproteinases and matrix degrading activity in vulnerable regions of human atherosclerotic plaques", *J. Clin. Invest.*, vol. 94, 1994, pp 2494–2503.

Henney A. M., et al., "Localization of stromelysin gene expression in atherosclerotic plaques by in situ hybridization", *Proc. Natl. Acad. Sci. U.S.A.*, vol. 88, 1991, pp 8154–8158.

Vine and Powell, "Metalloproteinases in degenerative aortic diseases", *Clin. Sci.*, vol. 81, 1991, pp 233–239.

Lee T. H., et al., "Impact of left ventricular cavity size on survival in advanced heart failure", *Am. J. Cardiol.*, vol. 72, 1993, pp 672–676.

Reddy H. K., et al., "Activated myocardial collagenase in idiopathic dilated cardiomyopathy: a marker of dilatation and remodeling", *Clin. Res*, vol. 41, No. 3, 1993, p 660A.

Tyagi S. C., et al., "Myocardial collagenase in failing human heart", *Clin. Res.*, vol. 41, No. 3, 1993, p 681 A.

Armstrong P. W., et al., "Structural remodelling in heart failure: gelatinase induction", *Can J. Cardiol.*, vol. 10, No. 2, 1994, pp 214–220.

Sabbah H. N., et al., "Left ventricular shape changes during the course of evolving heart failure", *Am. J. Physiol.*, vol. 263, 1992, pp H266–H270.

Bendeck M. P., et al., "Smooth muscle cell migration and matrix metalloproteinase expression after arterial injury in the rat", *Circulation Research*, vol. 75, No. 3, 1994, pp 539–545.

Pauly R. R., et al., "Migration of cultured vascular smooth muscle cells through a basement membrane barrier requires type IV collagenase activity and is inhibited by cellular differentiation", *Circulation Research*, vol. 75, No. 1, 1994, pp 41–54.

Davies M., et al., "Proteinases and glomerular matrix turnover", *Kidney Int.*, vol. 41, 1992, pp 671–678.

Martin J., et al., "Enhancement of glomerular mesangial cell neutral proteinase secretion by macrophages: role of interleukin 1", *J Immunol.*, vol. 137, No. 2, 1986, pp 525–529.

Marti H. P., et al., "Homology cloning of rat 72 kDa type IV collagenase: cytokine and second–messenger inducibility in glomerular mesangial cells", *Biochem. J.*, vol. 291, 1993, pp 441–446.

Marti H. P., et al., "Transforming growth factor–β1 stimulates glomerular mesangial cell synthesis of the 72–kd type IV collagenase", *Am. J. Pathol.*, vol. 144, No. 1, 1994, pp 82–94.

Bagchus W. M., et al., "Glomerulonephritis induced by monoclonal anti–thy 1.1 antibodies: A sequential histological and ultrastructural study in the rat", *Lab. Invest.*, vol. 55, No. 6, 1986, pp 680–687.

Lovett D. H., et al., "Structural characterization of the mesangial cell type IV collagenase and enhanced expression in a model of immune complex mediated glomerulonephritis" *Am. J. Pathol.*, vol. 141, No. 1, 1992, pp 85–98.

(List continued on next page.)

*Primary Examiner*—Richard L. Raymond
*Assistant Examiner*—Hong Liu
*Attorney, Agent, or Firm*—Charles W. Ashbrook

[57] ABSTRACT

The present invention relates to compounds of Formula I that inhibit matrix metalloproteinases and to a method of inhibiting matrix metalloproteinases using the compounds

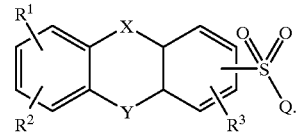

More particularly, the present invention relates to a method of treating diseases in which matrix metalloproteinases are involved such as multiple sclerosis, atherosclerotic plaque rupture, restenosis, aortic aneurysm, heart failure, periodontal disease, corneal ulceration, burns, decubital ulcers, chronic ulcers or wounds, cancer metastasis, tumor angiogenesis, osteoporosis, rheumatoid or osteoarthritis, renal disease, left ventricular dilatation, or other autoimmune or inflammatory diseases dependent upon tissue invasion by leukocytes.

28 Claims, No Drawings

OTHER PUBLICATIONS

Brown P. D., et al., "Independent expression and cellular processing of $M_r$ 72,000 type IV collagenase and interstitial collagenase in human tumorigenic cell lines", *Cancer Res.*, vol. 50, 1990, pp 6184–6191.

Kitamura M., et al., "Gene transfer of metalloproteinase transin induces aberrant behavior of cultured mesangial cells", *Kidney Int.*, vol. 45, 1994, pp 1580–1586.

Turck J., et al., "Matrix metalloproteinase 2 (gelatinase A) regulates glomerular mesangial cell proliferation and differentiation", *J. Biol. Chem.*, vol. 271, No. 25, 1996, pp 15074–15083.

Uitto V. J., et al., "Collagenase and neutral metallo–proteinase activity in extracts of inflamed human gingiva", *J. Periodontal Res.*, vol. 16, 1981, pp 417–424.

Overall C. M., et al., "Demonstration of tissue collagenase activity in vivo and its relationship to inflammation severity in human gingiva", *J. Periodontal Res.*, vol. 22, 1987, pp 81–88.

Brown S. I., et al., "Collagenolytic activity of alkali–burned corneas", *Arch. Ophthal.*, vol. 81, 1969, pp 370–373.

Burns F. R., et al., "Inhibition of purified collagenase from alkali–burned rabbit corneas", *Invest. Ophthalmol.*, vol. 30, No. 7, 1989, pp 1569–1575.

Saarialho–Kere U. K., et al., "Distinct populations of basal keratinocytes express stromelysin–1 and stromelysin–2 in chronic wounds", *J. Clin. Invest.*, vol. 94, 1994, pp 79–88.

Davies B., et al., "A synthetic matrix metalloproteinase inhibitor decreases tumor burden and prolongs survival of mice bearing human ovarian carcinoma xenografts", *Cancer Res.*, vol. 3, 1993, pp 2087–2091.

Melchiori A., et al., "Inhibition of tumor cell invasion by a highly conserved peptide sequence from the matrix metalloproteinase enzyme prosegment", *Cancer Res.*, vol. 52, 1992, pp 2353–2356.

DeClerck Y. A., et al., "Inhibition of invasion and metastasis in cells transfected with an inhibitor of metalloproteinases", *Cancer Res.*, vol. 52, 1992, pp 701–708.

Strongin A. Y., et al., "Plasma membrane–dependent activation of the 72–kDa type IV collagenase is prevented by complex formation with TIMP–2*", *J. Biol. Chem.*, vol. 268, No. 19, 1993, pp 14033–14039.

Monsky W. L., et al., "Binding and localization of $M_r$ 72,000 matrix metalloproteinase at cell surface invadopodia", *Cancer Res.*, vol. 53, 1993, pp 3159–3164.

Taraboletti G., et al., "Inhibition of angiogenesis and murine hemangioma growth by batimastat, a synthetic inhibitor of matrix metalloproteinases", *Journal of the National Cancer Institute*, vol. 87, No. 4, 1995, pp 293–298.

Benelli R., et al., "Inhibition of AIDS–Kaposi's sarcoma cell induced endothelial cell invasion by TIMP–2 and a synthetic peptide from the metalloproteinase propeptide: implications for an anti–angiogenic therapy", *Oncology Research*, vol. 6, No. 6, 1994, pp 251–257.

Walakovits L. A., et al., "Detection of stromelysin and collagenase in synovial fluid from patients with rheumatoid arthritis and post–traumatic knee injury", *Arthritis Rheum.*, vol. 35, No. 1, 1992, pp 35–42.

Zafarullah M., et al., "Elevated metalloproteinase and tissue inhibitor of metalloproteinase mRNA in human osteoarthritic synovia", *J. Rheumatol.*, vol. 20, No. 4, 1993, pp 693–697.

Andrews H. J., et al., "A synthetic peptide metalloproteinase inhibitor, but not Timp, prevents the breakdown of proteoglycan within articular cartilage in vitro", *Agents Actions*, vol. 37, 1992, pp 147–154.

Ellis A. J., et al., "The prevention of collagen breakdown in bovine nasal cartilage by Timp, Timp–2 and a low molecular weight synthetic inhibitor", *Biochem. Biophys. Res. Commun.*, vol. 201, No. 1, 1994, pp 94–101.

Gijbels K., et al., "Reversal of Experimental Autoimmune Encephalomyelitis with a hydroxamate inhibitor of matrix metalloproteases", *J. Clin. Invest.*, vol. 94, 1994, pp 2177–2182.

Romanic and Madri, " The induction of 72–kD Gelatinase in T cells upon adhesion of Endothelial cells is VCAM–1 Dependent", *J. Cell Biology*, vol. 125, No. 5, 1994, pp 1165–1178.

COMPOUNDS FOR AND METHODS OF INHIBITING MATRIX METALLOPROTEINASES

This application claims the benefit of U.S. Provisional Application No. 60/095,338 filed Aug. 4, 1998.

BACKGROUND OF THE INVENTION

1. Field of the Invention

The present invention relates to compounds that inhibit matrix metalloproteinases and to methods of inhibiting matrix metalloproteinases using the compounds. More particularly, the present invention relates to a method of treating diseases in which matrix metalloproteinases are involved such as multiple sclerosis, atherosclerotic plaque rupture, restenosis, aortic aneurysm, heart failure, periodontal disease, corneal ulceration, burns, decubital ulcers, chronic ulcers or wounds, cancer metastasis, tumor angiogenesis, osteoporosis, rheumatoid or osteoarthritis, renal disease, left ventricular dilatation, or other autoimmune or inflammatory diseases dependent upon tissue invasion by leukocytes.

2. Summary of the Related Art

The compounds of the present invention are inhibitors of the matrix metalloproteinases, e.g., stromelysin-1 (MMP-3) and gelatinase A (72 kDa gelatinase) (MMP-2).

Stromelysin-1 and gelatinase A are members of the matrix metalloproteinases (MMP) family. Other members include fibroblast collagenase (MMP-1), neutrophil collagenase, gelatinase B (92 kDa gelatinase) (MMP-9), stromelysin-2, stromelysin-3, matrilysin (MMP-7), collagenase 3 (MMP-1 3), and the newly discovered membrane-associated matrix metalloproteinases (Sato H., Takino T., Okada Y., Cao J., Shinagawa A., Yamamoto E., and Seiki M., *Nature*, 1994;370:61–65).

The catalytic zinc in matrix metalloproteinases is typically the focal point for inhibitor design. The modification of substrates by introducing zinc chelating groups has generated potent inhibitors such as peptide hydroxamates and thiol-containing peptides. Peptide hydroxamates and the natural endogenous inhibitors of MMPs (TIMPs) have been used successfully to treat animal models of cancer and inflammation.

The ability of the matrix metalloproteinases to degrade various components of connective tissue makes them potential targets for controlling pathological processes. For example, the rupture of atherosclerotic plaques is the most common event initiating coronary thrombosis. Destabilization and degradation of the extracellular matrix surrounding these plaques by MMPs has been proposed as a cause of plaque fissuring. The shoulders and regions of foam cell accumulation in human atherosclerotic plaques show locally increased expression of gelatinase B, stromelysin-1, and interstitial collagenase. In situ zymography of this tissue revealed increased gelatinolytic and caseinolytic activity (Galla Z. S., Sukhova G. K., Lark M. W., and Libby P., "Increased expression of matrix metalloproteinases and matrix degrading activity in vulnerable regions of human atherosclerotic plaques," *J. Clin. Invest.*, 1994;94:2494–2503). In addition, high levels of stromelysin RNA message have been found to be localized to individual cells in atherosclerotic plaques removed from heart transplant patients at the time of surgery (Henney A. M., Wakeley P. R., Davies M. J., Foster K., Hembry R., Murphy G., and Humphries S., "Localization of stromelysin gene expression in atherosclerotic plaques by in situ hybridization," *Proc. Nat'l. Acad. Sci.*, 1991;88:8154–8158).

Inhibitors of matrix metalloproteinases will have utility in treating degenerative aortic disease associated with thinning of the medial aortic wall. Increased levels of the proteolytic activities of MMPs have been identified in patients with aortic aneurysms and aortic stenosis (Vine N. and Powell J. T., "Metalloproteinases in degenerative aortic diseases," *Clin. Sci.*, 1991;81:233–239).

Heart failure arises from a variety of diverse etiologies, but a common characteristic is cardiac dilation which has been identified as an independent risk factor for mortality (Lee T. H., Hamilton M. A., Stevenson L. W., Moriguchi J. D., Fonarow G. C., Child J. S., Laks H., and Walden J. A., "Impact of left ventricular size on the survival in advanced heart failure," *Am. J. Cardiol.*, 1993;72:672–676). This remodeling of the failing heart appears to involve the breakdown of extracellular matrix. Matrix metalloproteinases are increased in patients with both idiopathic and ischemic heart failure (Reddy H. K., Tyagi S. C., Tjaha I. E., Voelker D. J., Campbell S. E., and Weber K. T., "Activated myocardial collagenase in idiopathic dilated cardiomyopathy," *Clin. Res.*, 1993;41:660A; Tyagi S. C., Reddy H. K., Voelker D., Tjara I. E., and Weber K. T., "Myocardial collagenase in failing human heart," *Clin. Res.*, 1993;41:681A). Animal models of heart failure have shown that the induction of gelatinase is important in cardiac dilation (Armstrong P. W., Moe G. W., Howard R. J., Grima E. A., and Cruz T. F., "Structural remodeling in heart failure: gelatinase induction," *Can. J. Cardiol.*, 1994;10:214–220), and cardiac dilation precedes profound deficits in cardiac function (Sabbah H. N., Kono T., Stein P. D., Mancini G. B., and Goldstein S., "Left ventricular shape changes during the course of evolving heart failure," *Am. J. Physiol.*, 1992;263:H266–H270).

Congestive heart failure (CHF) is a significant health care problem which currently accounts for 7% of total health care expenditures in the USA. Approximately 400,000 new cases of heart failure are identified annually. The primary cause for development of heart failure is ischemic heart disease, and most new cases occur after myocardial infarction. The number of hospital discharges for heart failure has increased from 377,000 in 1979 to 875,000 in 1993, and the number of deaths during the same period has risen 82.5%. The average mortality rate 8 years following initial diagnosis is 85% for men and 65% for women.

The development of CHF begins as an injurious process to the myocardium that reduces cardiac function (especially contractile or pump function) either in a specific region(s) or throughout its entire extent (i.e., globally). Heart failure is said to exist whenever the myocardial injury is of sufficient severity to reduce the heart's capacity to pump an adequate output of blood to satisfy the body's tissue requirements either at rest or during exercise. The disease state of heart failure is not a static situation, but instead progressively worsens until death occurs either suddenly (e.g., by cardiac arrhythmia or embolism to the brain or lung) or gradually from pump failure per se. The progressive decline in heart function in patients with CHF is characterized by progressive enlargement of the ventricular chambers (i.e., ventricular dilatation) and thinning and fibrosis of the ventricular muscle. The progressive ventricular enlargement and accompanying histologic changes in the ventricular muscle are termed "remodeling," a process that involves changes in myocardiocyte structure as well as changes in the amount and composition of the surrounding interstitial connective tissue. An important constituent of the interstitial connective tissue is a matrix of fibrillar collagen, the "tissue scaffolding" that contributes to the maintenance of proper ventricular geometry and structural alignment of adjoining cardiomyocytes. The interstitial collagen matrix is subject to increased dissolution and repair during "remodeling" that leads to ventricular enlargement and progressive heart failure. The deterioration of the collagen matrix is effected by increased activity of matrix metalloproteases, the inhibition of which is a new treatment for heart failure and ventricular dilatation. Ventricular dilatation, the severity of which is measured by the end-diastolic and end-systolic volumes, is a prognostic marker of the probability of subsequent morbidity and mortality. The larger the ventricular chamber dimensions, the greater the likelihood of subsequent morbid events. Not only is pump function impaired by remodeling and ventricular dilation, but the enlarged chambers are prone to formation of clots, which can lead to stroke or embolism to other major organs (e.g., kidney, legs, intestinal tract).

Standard treatment for heart failure utilizes diuretics to decrease fluid retention, angiotensin converting enzyme inhibitors (ACE-Is) to reduce cardiac workload on the failing heart via vasodilation, and in the final stages of failure the positive inotrope digitalis to maintain cardiac output. Although ACE-Is have the benefit of increasing longevity unlike diuretics or positive inotropes, the beneficial effect of ACE-Is is limited to delaying death by only about 18 months. Clinical trials with β-adrenergic blockers were recently conducted based on the hypothesis that reducing sympathetic drive would decrease the metabolic load on heart muscle cells. Unfortunately, this class of compounds was also found to not have a substantial effect on the progression of heart failure. The failure or limited success of previous heart failure therapies clearly shows that the controlling mechanism(s) mediating heart failure has not been targeted.

Drug development of the treatment of heart failure since the 1960s has focussed on cardiac muscle cells. The goal has been to reduce the workload on the cells, improve blood flow to the cells, increase the contraction of the muscle, decrease the metabolic demand on cardiac myocytes, or some combination of these by various means. Focus on cardiac myocytes may have served to focus attention too far downstream. Overt heart failure may be caused by the breakdown of cardiac connective tissue. The breakdown in cardiac connective tissue proteins thus mediates cardiac dilation, one of the earliest characteristics of heart failure.

We have now discovered that compounds which inhibit MMPs that mediate the breakdown of connective tissues are useful for treating heart failure and associated ventricular dilatation.

Neointimal proliferation, leading to restenosis, frequently develops after coronary angioplasty. The migration of vascular smooth muscle cells (VSMCs) from the tunica media to the neointima is a key event in the development and progression of many vascular diseases and a highly predictable consequence of mechanical injury to the blood vessel (Bendeck M. P., Zempo N., Clowes A. W., Galardy R. E., and Reidy M., "Smooth muscle cell migration and matrix metalloproteinase expression after arterial injury in the rat," Circulation Research, 1994;75:539–545). Northern blotting and zymographic analyses indicated that gelatinase A was the principal MMP expressed and excreted by these cells. Further, antisera capable of selectively neutralizing gelatinase A activity also inhibited VSMC migration across basement membrane barrier. After injury to the vessel, gelatinase A activity increased more than 20-fold as VSMCs underwent the transition from a quiescent state to a proliferating, motile phenotype (Pauly R. R., Passaniti A., Bilato C., Monticone R., Cheng L., Papadopoulos N., Gluzband Y. A., Smith L., Weinstein C., Lakatta E., and Crow M. T., "Migration of cultured vascular smooth muscle cells through a basement membrane barrier requires type IV collagenase activity and is inhibited by cellular differentiation," Circulation Research, 1994;75:41–54).

Normal kidney function is dependent on the maintenance of tissues constructed from differentiated and highly specialized renal cells which are in a dynamic balance with their surrounding extracellular matrix (ECM) components (Davies M. et al., "Proteinases and glomerular matrix turnover," Kidney Int., 1992;41:671–678). Effective glomerular filtration requires that a semi-permeable glomerular basement membrane (GBM) composed of collagens, fibronectin, enactin, laminin and proteoglycans is maintained. A structural equilibrium is achieved by balancing the continued deposition of ECM proteins with their degradation by specific metalloproteinases (MMP). These proteins are first secreted as proenzymes and are subsequently activated in the extracellular space. These proteinases are in turn subject to counter balancing regulation of their activity by naturally occurring inhibitors referred to as TIMPs (tissue inhibitors of metalloproteinases).

Deficiency or defects in any component of the filtration barrier may have catastrophic consequences for longer term renal function. For example, in hereditary nephritis of Alport's type, associated with mutations in genes encoding ECM proteins, defects in collagen assembly lead to progressive renal failure associated with splitting of the GBM and eventual glomerular and interstitial fibrosis. By contrast in inflammatory renal diseases such as glomerulonephritis, cellular proliferation of components of the glomerulus often precede obvious ultrastructural alteration of the ECM matrix. Cytokines and growth factors implicated in proliferative glomerulonephritis such as interleukin-1, tumor necrosis factor, and transforming growth factor beta can upregulate metalloproteinase expression in renal mesangial cells (Martin J. et al., "Enhancement of glomerular mesangial cell neutral proteinase secretion by macrophages: role of interleukin 1," J. Immunol., 1986;137:525–529; Marti H. P. et al., "Homology cloning of rat 72 kDa type IV collagenase: Cytokine and second-messenger inducibility in mesangial cells," Biochem. J., 1993;291:441–446; Marti H. P. et al., "Transforming growth factor-b stimulates glomerular mesangial cell synthesis of the 72 kDa type IV collagenase," Am. J. Pathol., 1994;144:82–94). These metalloproteinases are believed to be intimately involved in the aberrant tissue remodeling and cell proliferation characteristic of renal diseases, such as, IgA nephropathy which can progress to through a process of gradual glomerular fibrosis and loss of functional GBM to end-stage renal disease. Metalloproteinase expression has already been well-characterized in experimental immune complex-mediated glomerulonephritis such as the anti-Thy 1.1 rat model (Bagchus W. M., Hoedemaeker P. J., Rozing J., Bakker W. W., "Glomerulonephritis induced by monoclonal anti-Thy 1.1 antibodies: A sequential histological and ultrastructural study in the rat," Lab. Invest., 1986;55:680–687; Lovett D. H., Johnson R. J., Marti H. P., Martin J., Davies M., Couser W. G., "Structural characterization of the mesangial cell type IV collagenase and enhanced expression in a model of immune complex mediated glomerulonephritis," Am. J. Pathol., 1992;141:85–98).

Unfortunately at present, there are very limited therapeutic strategies for modifying the course of progressive renal disease. Although many renal diseases have an inflammatory component, their responses to standard immunosuppressive regimes are unpredictable and potentially hazardous to individual patients. The secondary consequences of gradual nephron failure such as activation of the renin-angiotensin system, accompanied by individual nephron glomerular hyperfiltration and renal hypertension, may be effectively treated with ACE inhibitors or angiotensin II receptor antagonists; but at best, these compounds can only reduce the rate of GFR decline.

A novel strategy to treat at least some renal diseases has been suggested by recent observations of MMP behavior. A rat mesangial cell MMP has been cloned (MMP-2) which is regulated in a tissue specific manner, and in contrast to other cellular sources such as tumor cell lines, is induced by cytokines (Brown P. D., Levy A. T., Margulies I., Liotta L. A., Stetler-Stevenson W. G., "Independent expression and cellular processing of Mr 72,000 type IV collagenase and interstitial collagenase in human tumorigenic cell lines," *Cancer Res.*, 1990;50:6184–6191; Marti H. P. et al., "Homology cloning of rat 72 kDa type IV collagenase: Cytokine and second-messenger inducibility in mesangial cells," *Biochem. J.*, 1993;291:441–446). While MMP-2 can specifically degrade surrounding ECM, it also affects the phenotype of adjacent mesangial cells. Inhibition of MMP-2 by antisense oligonucleotides or transfection techniques can induce a reversion of the proliferative phenotype of cultured mesangial cells to a quiescent or non-proliferative phenotype mimicking the natural in vitro behavior of these cells (Kitamura M. et al., "Gene transfer of metalloproteinase transin induces aberrant behaviour of cultured mesangial cells," *Kidney Int.*, 1994;45:1580–1586; Turck J. et al., "Matrix metalloproteinase 2 (gelatinase A) regulates glomerular mesangial cell proliferation and differentiation," *J. Biol. Chem.*, 1996;271:15074–15083).

Collagenase and stromelysin activities have been demonstrated in fibroblasts isolated from inflamed gingiva (Uitto V. J., Applegren R., and Robinson P. J., "Collagenase and neutral metalloproteinase activity in extracts from inflamed human gingiva," *J. Periodontal Res.*, 1981;16:417–424), and enzyme levels have been correlated to the severity of gum disease (Overall C. M., Wiebkin O. W., and Thonard J. C., "Demonstrations of tissue collagenase activity in vivo and its relationship to inflammation severity in human gingiva," *J. Periodontal Res.*, 1987;22:81–88). Proteolytic degradation of extracellular matrix has been observed in corneal ulceration following alkali burns (Brown S. I., Weller C. A., and Wasserman H. E., "Collagenolytic activity of alkali burned corneas," *Arch. Opthalmol.*, 1969;81:370–373). Thiol-containing peptides inhibit the collagenase isolated from alkali-burned rabbit corneas (Burns F. R., Stack M. S., Gray R. D., and Paterson C. A., *Invest. Opththamol.*, 1989;30:1569–1575).

Stromelysin is produced by basal keratinocytes in a variety of chronic ulcers (Saarialho-Kere U. K., Ulpu K., Pentland A. P., Birkedal-Hansen H., Parks W. C., Welgus H. G., "Distinct populations of basal keratinocytes express stromelysin-1 and stromelysin-2 in chronic wounds," *J. Clin. Invest.*, 1994;94:79–88).

Stromelysin-1 mRNA and protein were detected in basal keratinocytes adjacent to but distal from the wound edge in what probably represents the sites of proliferating epidermis. Stromelysin-1 may thus prevent the epidermis from healing.

Davies et al., (*Cancer Res.*, 1993;53:2087–2091) reported that a peptide hydroxamate, BB-94, decreased the tumor burden and prolonged the survival of mice bearing human ovarian carcinoma xenografts. A peptide of the conserved MMP propeptide sequence was a weak inhibitor of gelatinase A and inhibited human tumor cell invasion through a layer of reconstituted basement membrane (Melchiori A., Albili A., Ray J. M., and Stetler-Stevenson W. G., *Cancer Res.*, 1992;52:2353–2356), and the natural tissue inhibitor of metalloproteinase-2 (TIMP-2) also showed blockage of tumor cell invasion in in vitro models (DeClerck Y. A., Perez N., Shimada H., Boone T. C., Langley K. E., and Taylor S. M., *Cancer Res.*, 1992;52:701–708). Studies of human cancers have shown that gelatinase A is activated on the invasive tumor cell surface (Strongin A. Y., Marmer B. L., Grant G. A., and Goldberg G. I., *J. Biol. Chem.*, 1993;268:14033–14039) and is retained there through interaction with a receptor-like molecule (Monsky W. L., Kelly T., Lin C. Y., Yeh Y., Stetler-Stevenson W. G., Mueller S. C., and Chen W. T., *Cancer Res.*, 1993;53:3159–3164).

Inhibitors of MMPs have shown activity in models of tumor angiogenesis (Taraboletti G., Garofalo A., Belotti D., Drudis T., Borsotti P., Scanziani E., Brown P. D., and Giavazzi R., *Journal of the National Cancer Institute*, 1995;87:293; and Benelli R., Adatia R., Ensoli B., Stetler-Stevenson W. G., Santi L., and Albini A., *Oncology Research*, 1994;6:251–257).

Several investigators have demonstrated consistent elevation of stromelysin and collagenase in synovial fluids from rheumatoid and osteoarthritis patients as compared to controls (Walakovits L. A., Moore V. L., Bhardwaj N., Gallick G. S., and Lark M. W., "Detection of stromelysin and collagenase in synovial fluid from patients with rheumatoid arthritis and post-traumatic knee injury," *Arthritis Rheum.*, 1992;35:35–42; Zafarullah M., Pelletier J. P., Cloutier J. M., and Marcel-Pelletier J., "Elevated metalloproteinases and tissue inhibitor of metalloproteinase mRNA in human osteoarthritic synovia," *J. Rheumatol.*, 1993;20:693–697). TIMP-1 and TIMP-2 prevented the formation of collagen fragments, but not proteoglycan fragments, from the degradation of both the bovine nasal and pig articular cartilage models for arthritis, while a synthetic peptide hydroxamate could prevent the formation of both fragments (Andrews H. J., Plumpton T. A., Harper G. P., and Cawston T. E., *Agents Actions*, 1992;37:147–154; Ellis A. J., Curry V. A., Powell E. K., and Cawston T. E., *Biochem. Biophys. Res. Commun.*, 1994;201:94–101).

Gijbels et al., (*J. Clin. Invest.*, 1994;94:2177–2182) recently described a peptide hydroxamate, GM6001, that suppressed the development or reversed the clinical expression of experimental allergic encephalomyelitis (EAE) in a dose dependent manner, suggesting the use of MMP inhibitors in the treatment of autoimmune inflammatory disorders such as multiple sclerosis.

A recent study by Madri has elucidated the role of gelatinase A in the extravasation of T-cells from the blood stream during inflammation (Ramanic A. M. and Madri J. A., "The Induction of 72-kD Gelatinase in T Cells upon Adhesion to Endothelial Cells is VCAM-1 Dependent," *J. Cell Biology*, 1994;125:1165–1178). This transmigration past the endothelial cell layer is coordinated with the induction of gelatinase A and is mediated by binding to the vascular cell adhesion molecule-1 (VCAM-1). Once the barrier is compromised, edema and inflammation are produced in the CNS. Leukocytic migration across the blood-brain barrier is known to be associated with the inflammatory response in EAE. Inhibition of the metalloproteinase gelatinase A would block the degradation of extracellular matrix by activated T-cells that is necessary for CNS penetration.

These studies provided the basis for the belief that an inhibitor of stromelysin-1 and/or gelatinase A will treat diseases involving disruption of extracellular matrix resulting in inflammation due to lymphocytic infiltration, inappropriate migration of metastatic or activated cells, or loss of structural integrity necessary for organ function.

WO 97/00675 discloses compounds of the formula:

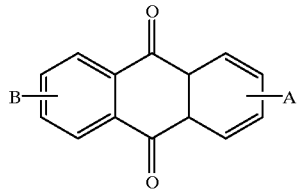

wherein B can be H and A can be —SO$_2$R$^1$, wherein R$^1$ is —NR$^2$R$^3$ and R$^2$ can be H and R$^3$ is a group containing a carboxylic acid radical. The compounds are disclosed as agents for the treatment of pathologies in which the erosion of the cartilaginous and bone matrix occurs.

EP 0 307 879 discloses compounds of the formula:

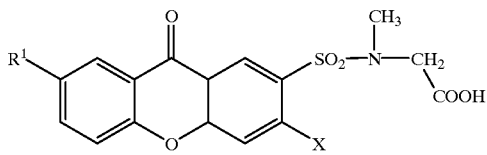

wherein R$^1$ is a trihalomethyl, a carboxy moiety, or a sulfonamido, and X is alkyl, alkoxy, or halo. The compounds are disclosed as being inhibitors of the aldose reductase enzyme system.

We have identified a series of [6,6,6]-tricyclic sulfonamide derivatives that are inhibitors of matrix metalloproteinases, particularly stromelysin-1 and gelatinase A, and thus useful as agents for the treatment of multiple sclerosis, atherosclerotic plaque rupture, restenosis, aortic aneurysm, heart failure, periodontal disease, corneal ulceration, burns, decubital ulcers, chronic ulcers or wounds, cancer metastasis, tumor angiogenesis, osteoporosis, rheumatoid or osteoarthritis, renal disease, left ventricular dilatation, or other autoimmune or inflammatory diseases dependent upon tissue invasion by leukocytes.

SUMMARY OF THE INVENTION

The present invention provides compounds of Formula I:

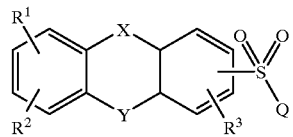

and pharmaceutically acceptable salts thereof, wherein X and Y are independently O, S(O)$_n$, CH$_2$, C=O, NH, or NC$_1$–C$_6$ alkyl, provided that X and Y are not both $$-\overset{O}{\underset{\|}{C}}-\ ;$$

n is 0, 1, or 2, each R$^1$, R$^2$, and R$^3$ are independently halogen, hydrogen, —NO$_2$, —NH$_2$, —NH(C$_1$–C$_6$alkyl), —N(C$_1$–C$_6$alkyl)$_2$, —CN, —CF$_3$, —C$_1$–C$_6$ alkyl, —C$_1$–C$_6$ alkoxy, —CO$_2$H, or —CO$_2$C$_1$–C$_6$ alkyl;

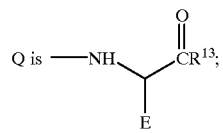

E is

—(CH$_2$)$_m$—NH—Z—R$^{10}$,

—(CH$_2$)$_m$—S—C(phenyl)$_3$,

—(CH$_2$)$_m$—O—(CH$_2$)$_l$-phenyl,

—(CH$_2$)$_m$—O—C$_1$–C$_6$ alkyl,

—(CH$_2$)$_m$—OH,

—(CH$_2$)$_m$—SH,

—(CH$_2$)$_m$-aryl,

—(CH$_2$)$_m$-heteroaryl,

—(CH$_2$)$_m$—NHC(=NH)NH$_2$, $$-(CH_2)_{\overline{m}}-\overset{O}{\underset{\|}{C}}R^{10},$$

—(CH$_2$)$_m$S(O)$_n$—C$_1$–C$_6$ alkyl,

C$_1$–C$_6$ alkyl, aryl,

—(CH$_2$)$_m$-cycloalkyl,

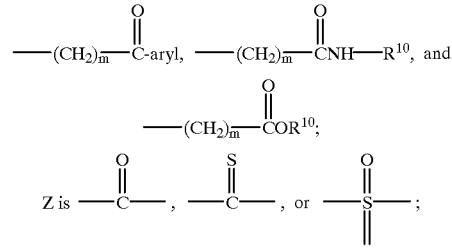

m is 1 to 6;

l is 1 to 6;

R$^{10}$ is

—(CR$^{11}$R$^{12}$)$_m$—S-aryl,

—(CR$^{11}$R$^{12}$)$_m$—S-heteroaryl,

—(CR$^{11}$R$^{12}$)$_m$—O-aryl,

—(CR$^{11}$R$^{12}$)$_m$—O-heteroaryl,

—(CR$^{11}$R$^{12}$)$_m$-aryl,

—(CH$_2$)$_m$—C$_2$–C$_8$ cycloalkenyl,

—(CH$_2$)$_m$-heteroaryl,

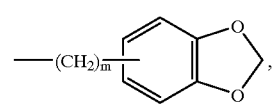

—$(CH_2)_m$—NH-aryl,

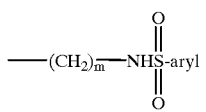

—$C_2$–$C_8$ cycloalkyl,
—$(CH_2)_m$—C(phenyl)$_3$,
—$(CH_2)_m$—NR$^{11}$R$^{12}$,
—$C_1$–$C_6$ alkenyl-phenyl,
-cycloalkyl-phenyl,

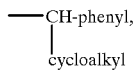

$C_1$–$C_6$ alkyl,
aryl,
heteroaryl, or
—$(CH_2)_m$—CH(phenyl)$_2$;
each R$^{11}$ and R$^{12}$ are independently hydrogen, $C_1$–$C_6$ alkyl, or benzyl; and R$^{13}$ is —OR$^{11}$ or —NHOR$^{11}$.

In a preferred embodiment of the compounds of Formula I, Q is D-alanine, D-valine, D-leucine, D-isoleucine, D-phenylalanine, D-proline, D-serine, D-threonine, D-tyrosine, D-asparagine, D-glutamine, D-lysine, D-arginine, D-tryptophan, D-histidine, D-cysteine, D-methionine, D-aspartic acid, D-glutamic acid, or D-homophenylalanine.

In another preferred embodiment of the compounds of Formula I, Q is L-alanine, L-valine, L-leucine, L-isoleucine, L-phenylalanine, L-proline, L-serine, L-threonine, L-tyrosine, L-asparagine, L-glutamine, L-lysine, L-arginine, L-tryptophan, L-histidine, L-cysteine, L-methionine, L-aspartic acid, L-glutamic acid, or L-homophenylalanine.

In a more preferred embodiment, the present invention provides the compounds:

(2S)-3-Methyl-2-((thianthren-2-ylsulfonyl)amino)butanoic acid;
(2S)-4-Phenyl-2-((phenoxathiin-3-ylsulfonyl)amino) butanoic acid;
(S)-4-Phenyl-2-(9H-xanthene-2-sulfonylamino)-butyric acid;
(S)-3-Methyl-2-(phenoxathiine-2-sulfonylamino)-butyric acid;
(S)-3-Hydroxy-2-(phenoxathiine-2-sulfonylamino)-propionic acid;
(S)-3-Hydroxy-2-(9H-xanthene-2-sulfonylamino)-propionic acid;
(S)-2-(10,10-Dioxo-10H-10$\lambda^6$-phenoxathiine-2-sulfonylamino)-4-phenyl-butyric acid;
(R)-3-Methyl-2-(phenoxathiine-2-sulfonylamino)-butyric acid;
(S)-2-(Phenoxathiine-2-sulfonylamino)-propionic acid;
(S)-4-Methanesulfinyl-2-(phenoxathiine-2-sulfonylamino)-butyric acid;
(S)-4-Methyl-2-(phenoxathiine-2-sulfonylamino)-pentanoic acid;
(S)-2-(Phenoxathiine-2-sulfonylamino)-3-phenyl-propionic acid;
(R)-2-(Phenoxathiine-2-sulfonylamino)-3-tritylsulfanyl-propionic acid;
(S)-3-(4-Hydroxy-phenyl)-2-(phenoxathiine-2-sulfonylamino)-propionic acid;
(S)-3-(1H-Indol-3-yl)-2-(phenoxathiine-2-sulfonylamino)-propionic acid;
(S)-2-(Phenoxathiine-2-sulfonylamino)-succinamic acid;
(S)-(Phenoxathiine-2-sulfonylamino)-phenyl-acetic acid;
(S)-N-Hydroxy-3-methyl-2-((thianthren-2-ylsulfonyl) amino)butanamide;
(S)-N-Hydroxy-2-(phenoxathiine-2-sulfonylamino)-4-phenyl-butyramide;
(S)-N-Hydroxy-4-phenyl-2-(9H-xanthene-2-sulfonylamino)-butyramide;
(S)-N-Hydroxy-3-methyl-2-(phenoxathiine-2-sulfonylamino)-butyramide;
(S)-N-Hydroxy-3-hydroxy-2-(phenoxathiine-2-sulfonylamino)-propionamide;
(S)-N-Hydroxy-3-hydroxy-2-(9H-xanthene-2-sulfonylamino)-propionamide;
(S)-N-Hydroxy-2-(10,10-dioxo-10H-10$\lambda^6$-phenoxathiine-2-sulfonylamino)-4-phenyl-butyramide;
(R)-N-Hydroxy-3-methyl-2-(phenoxathiine-2-sulfonylamino)-butyramide;
(S)-N-Hydroxy-2-(phenoxathiine-2-sulfonylamino)-propionamide;
(S)-N-Hydroxy-4-methanesulfinyl-2-(phenoxathiine-2-sulfonylamino)-butyramide;
(S)-N-Hydroxy-4-methyl-2-(phenoxathiine-2-sulfonylamino)-pentanamide;
(S)-N-Hydroxy-2-(phenoxathiine-2-sulfonylamino)-3-phenyl-propionamide;
(R)-N-Hydroxy-2-(phenoxathiine-2-sulfonylamino)-3-tritylsulfanyl-propionamide;
(S)-N-Hydroxy-3-(4-hydroxy-phenyl)-2-(phenoxathiine-2-sulfonylamino)-propionamide;
(S)-N-Hydroxy-3-(1H-indol-3-yl)-2-(phenoxathiine-2-sulfonylamino)-propionamide;
(S)-N-Hydroxy-2-(phenoxathiine-2-sulfonylamino)-succinamide;
(S)-N-Hydroxy-(phenoxathiine-2-sulfonylamino)-phenyl-acetamide;
(R)-N-Hydroxy-2-(phenoxathiine-2-sulfonylamino)-4-phenyl-butyramide;
(R)-N-Hydroxy-4-phenyl-2-(9H-xanthene-2-sulfonylamino)-butyramide;
(S)-N-Hydroxy-3-methyl-2-(9H-xanthene-2-sulfonylamino)-butyramide;
(R)-N-Hydroxy-3-hydroxy-2-(phenoxathiine-2-sulfonylamino)-propionamide;
(R)-N-Hydroxy-3-hydroxy-2-(9H-xanthene-2-sulfonylamino)-propionamide;
(S)-N-Hydroxy-3-hydroxy-2-(9H-xanthene-2-sulfonylamino)-propionamide;
(S)-2-(10,10-Dioxo-10H-10$\lambda^6$-phenoxathiine-2-sulfonylamino)-N-hydroxy-4-phenyl-butyramide;
(R)-2-(10,10-Dioxo-10H-10$\lambda^6$-phenoxathiine-2-sulfonylamino)-N-hydroxy-4-phenyl-butyramide;
(R)-N-Hydroxy-2-(phenoxathiine-2-sulfonylamino)-propionamide;
(S)-N-Hydroxy-2-(9H-xanthene-2-sulfonylamino)-propionamide;
(R)-N-Hydroxy-2-(9H-xanthene-2-sulfonylamino)-propionamide;
(S)-N-Hydroxy-2-(phenoxathiine-3-sulfonylamino)-succinamide;
(R)-N-Hydroxy-2-(phenoxathiine-3-sulfonylamino)-succinamide;
(R)-N-Hydroxy-2-(9H-xanthene-3-sulfonylamino)-succinamide;
(S)-N-Hydroxy-2-(9H-xanthene-3-sulfonylamino)-succinamide;

(R)-2-(10,10-Dioxo-10H-10λ⁶-phenoxathiine-3-sulfonylamino)-N-hydroxy-succinamide;
(S)-2-(10,10-Dioxo-10H-10λ⁶-phenoxathiine-3-sulfonylamino)-N-hydroxy-succinamide;
(S)-2-(10,10-Dioxo-10H-10λ⁶-phenoxathiine-2-sulfonylamino)-N-hydroxy-propionic acid;
(R)-2-(10,10-Dioxo-10H-10λ⁶-phenoxathiine-2-sulfonylamino)-N-hydroxy-propionamide;
(R)-2-(10,10-Dioxo-10H-10λ⁶-phenoxathiine-2-sulfonylamino)-N-hydroxy-3-hydroxy-propionamide;
(S)-2-(10,10-Dioxo-10H-10λ⁶-phenoxathiine-2-sulfonylamino)-N-hydroxy-3-hydroxy-propionamide;
(S)-2-(10,10-Dioxo-10H-10λ⁶-phenoxathiine-2-sulfonylamino)-N-hydroxy-3-methyl-butyramide;
(R)-2-(10,10-Dioxo-10H-10λ⁶-phenoxathiine-2-sulfonylamino)-N-hydroxy-3-methyl-butyramide;
(S)-N-Hydroxy-2-(10,10-dioxo-10H-10λ⁶-phenoxathiine-2-sulfonylamino)-4-phenyl-butyramide;
(S)-3-Benzyloxy-N-hydroxy-2-(phenoxathiine-2-sulfonylamino)-propionamide;
(R)-3-Benzyloxy-N-hydroxy-2-(phenoxathiine-2-sulfonylamino)-propionamide;
(S)-3-Benzyloxy-N-hydroxy-2-(10,10-dioxo-10H-10λ⁶-phenoxathiine-2-sulfonylamino)-propionamide;
(R)-3-Benzyloxy-N-hydroxy-2-(10,10-dioxo-10H-10λ⁶-phenoxathiine-2-sulfonylamino)-propionamide;
(S)-3-Benzyloxy-N-hydroxy-2-(9H-xanthene-2-sulfonylamino)-propionamide;
(R)-3-Benzyloxy-N-hydroxy-2-(9H-xanthene-2-sulfonylamino)-propionamide;
(R)-2-(Phenoxathiine-2-sulfonylamino)-4-phenyl-butyric acid;
(R)-4-Phenyl-2-(9H-xanthene-2-sulfonylamino)-butyric acid;
(S)-3-Methyl-2-(9H-xanthene-2-sulfonylamino)-butyric acid;
(R)-3-Hydroxy-2-(phenoxathiine-2-sulfonylamino)-propionic acid;
(R)-3-Hydroxy-2-(9H-xanthene-2-sulfonylamino)-propionic acid;
(S)-3-Hydroxy-2-(9H-xanthene-2-sulfonylamino)-propionic acid;
(S)-2-(10,10-Dioxo-10H-10λ⁶-phenoxathiine-2-sulfonylamino)-4-phenyl-butyric acid;
(R)-2-(10,10-Dioxo-10H-10λ⁶-phenoxathiine-2-sulfonylamino)-4-phenyl-butyric acid;
(R)-2-(Phenoxathiine-2-sulfonylamino)-propionic acid;
(S)-2-(9H-Xanthene-2-sulfonylamino)-propionic acid;
(R)-2-(9H-Xanthene-2-sulfonylamino)-propionic acid;
(S)-2-(Phenoxathiine-3-sulfonylamino)-succinic acid;
(R)-2-(Phenoxathiine-3-sulfonylamino)-succinic acid;
(R)-2-(9H-Xanthene-3-sulfonylamino)-succinic acid;
(S)-2-(9H-Xanthene-3-sulfonylamino)-succinic acid;
(R)-2-(10,10-Dioxo-10H-10λ⁶-phenoxathiine-3-sulfonylamino)-succinic acid;
(S)-2-(10,10-Dioxo-10H-10λ⁶-phenoxathiine-3-sulfonylamino)-succinic acid;
(S)-2-(10,10-Dioxo-10H-10λ⁶-phenoxathiine-2-sulfonylamino)-propionic acid;
(R)-2-(10,10-Dioxo-10H-10λ⁶-phenoxathiine-2-sulfonylamino)-propionic acid;
(R)-2-(10,10-Dioxo-10H-10λ⁶-phenoxathiine-2-sulfonylamino)-3-hydroxy-propionic acid;
(S)-2-(10,10-Dioxo-10H-10λ⁶-phenoxathiine-2-sulfonylamino)-3-hydroxy-propionic acid;
(S)-2-(10,10-Dioxo-10H-10λ⁶-phenoxathiine-2-sulfonylamino)-3-methyl-butyric acid;
(R)-2-(10,10-Dioxo-10H-10λ⁶-phenoxathiine-2-sulfonylamino)-3-methyl-butyric acid;
(S)-3-Benzyloxy-2-(phenoxathiine-2-sulfonylamino)-propionic acid;
(R)-3-Benzyloxy-2-(phenoxathiine-2-sulfonylamino)-propionic acid;
(S)-3-Benzyloxy-2-(10,10-dioxo-10H-10λ⁶-phenoxathiine-2-sulfonylamino)-propionic acid;
(R)-3-Benzyloxy-2-(10,10-dioxo-10H-10λ⁶-phenoxathiine-2-sulfonylamino)-propionic acid;
(S)-3-Benzyloxy-2-(9H-xanthene-2-sulfonylamino)-propionic acid; and
(R)-3-Benzyloxy-2-(9H-xanthene-2-sulfonylamino)-propionic acid.

Also provided is a method of inhibiting a matrix metalloproteinase in a patient in need of matrix metalloproteinase inhibition, the method comprising administering to the patient a therapeutically effective amount of a compound of Formula I.

Also provided is a method of treating multiple sclerosis, the method comprising administering to a patient having multiple sclerosis a therapeutically effective amount of a compound of Formula I.

Also provided is a method of treating atherosclerotic plaque rupture, the method comprising administering to a patient having an atherosclerotic plaque at risk for rupture a therapeutically effective amount of a compound of Formula I.

Also provided is a method of treating or preventing restenosis, the method comprising administering to a patient having restenosis or at risk of having restenosis a therapeutically effective amount of a compound of Formula I.

Also provided is a method of treating aortic aneurysm, the method comprising administering to a patient having aortic aneurysm a therapeutically effective amount of a compound of Formula I.

Also provided is a method of treating heart failure, the method comprising administering to a patient having heart failure a therapeutically effective amount of a compound of Formula I.

Also provided is a method of treating periodontal disease, the method comprising administering to a patient having periodontal disease a therapeutically effective amount of a compound of Formula I.

Also provided is a method of treating corneal ulceration, the method comprising administering to a patient having corneal ulceration a therapeutically effective amount of a compound of Formula I.

Also provided is a method of treating burns, the method comprising administering to a patient having burns a therapeutically effective amount of a compound of Formula I.

Also provided is a method of treating decubital ulcers, the method comprising administering to a patient having decubital ulcers a therapeutically effective amount of a compound of Formula I.

Also provided is a method of treating chronic ulcers or wounds, the method comprising administering to a patient having chronic ulcers or wounds a therapeutically effective amount of a compound of Formula I.

Also provided is a method of treating cancer metastasis, the method comprising administering to a patient having cancer a therapeutically effective amount of a compound of Formula I.

Also provided is a method of treating tumor angiogenesis, the method comprising administering to a patient having tumor angiogenesis a therapeutically effective amount of a compound of Formula I.

Also provided is a method of treating arthritis, the method comprising administering to a patient having arthritis a therapeutically effective amount of a compound of Formula I.

In a more preferred embodiment, the arthritis is rheumatoid arthritis.

In another more preferred embodiment, the arthritis is osteoarthritis.

Also provided is a method of treating osteoporosis, the method comprising administering to a patient having osteoporosis a therapeutically effective amount of a compound of Formula I.

Also provided is a method of treating renal disease, the method comprising administering to a patient having renal disease a therapeutically effective amount of a compound of Formula I.

Also provided is a method of treating left ventricular dilatation, the method comprising administering to a patient having left ventricular dilatation a therapeutically effective amount of a compound of Formula I.

Also provided is a method of treating autoimmune or inflammatory diseases dependent upon tissue invasion by leukocytes, the method comprising administering to a patient having autoimmune or inflammatory diseases dependent upon tissue invasion by leukocytes a therapeutically effective amount of a compound of Formula I.

In a preferred embodiment of the compounds of Formula I, the group

is located at the 2- or 3-position.

DETAILED DESCRIPTION OF THE INVENTION

The term "alkoxy" means an alkyl group attached to an oxygen atom. Representative examples of alkoxy groups include methoxy, ethoxy, tert-butoxy, propoxy, and isobutoxy.

The term "halogen" includes chlorine, fluorine, bromine, and iodine.

The term "aryl" means an aromatic hydrocarbon. Representative examples of aryl groups include phenyl and naphthyl.

The term "phenyl" also includes substituted phenyl wherein one or more hydrogen atom on the phenyl ring is replaced with an organic radical. Examples of suitable substituents include, but are not limited to, halogen, $C_1$–$C_6$ alkoxy, —$CF_3$, —$NO_2$, —CN, —$NH_2$, —NH($C_1$–$C_6$ alkyl), or —N($C_1$–$C_6$ alkyl)$_2$.

The term "heteroaryl" means an aryl group wherein one or more carbon atom of the aromatic hydrocarbon has been replaced with a heteroatom. Examples of heteroaryl groups include, but are not limited to, 2- or 3-thienyl, 2- or 3-furanyl, 2- or 3-pyrrolyl, 2-, 3-, or 4-pyridinyl, 2-pyrazinyl, 2-, 4-, or 5-pyrimidinyl, 3- or 4-pyridazinyl, or 2-, 3-, 4-, 5-, 6-, or 7-indolyl.

The term "alkyl" means a straight or branched chain hydrocarbon. Representative examples of alkyl groups are methyl, ethyl, propyl, isopropyl, isobutyl, butyl, tert-butyl, sec-butyl, pentyl, and hexyl.

The term "alkene" means a straight or branched hydrocarbon having one or more carbon-carbon double bond.

The term "cycloalkyl" means a cyclic hydrocarbon. Examples of cycloalkyl groups include cyclopropane, cyclobutane, cyclopentane, cyclohexane, and cyclooctane.

The term "heteroatom" includes oxygen, nitrogen, and sulfur.

The aryl or heteroaryl groups may be substituted with one or more substituents, which can be the same or different. Examples of suitable substituents include alkyl, alkoxy, thioalkoxy, hydroxy, halogen, trifluoromethyl, amino, alkylamino, dialkylamino, —$NO_2$, —CN, —$CO_2H$, —$CO_2$ alkyl, —$SO_3H$, —CHO, —CO alkyl, —$CONH_2$, —CONH-alkyl, —$CONHR^q$, —CON(alkyl)$_2$, —$(CH_2)_n$—$NH_2$, where n is 1 to 5 and —$(CH_2)_n$—NH-alkyl, —$NHR^q$, or —$NHCOR^q$, and $R^q$ is hydrogen or alkyl.

The symbol "—" means a bond.

The group Q in Formula I is attached via the nitrogen of the amino acid to the group

Also, in a preferred embodiment, the group

is attached at the 2- or 3-position of the tricyclic ring system as follows:

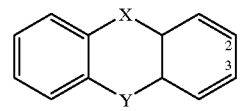

The compounds of Formula I can be administered to a patient either alone or as part of a pharmaceutically acceptable composition. The compositions can be administered to patients such as humans and animals either orally, rectally, parenterally (intravenously, intramuscularly, or subcutaneously), intracisternally, intravaginally, intraperitoneally, intravesically, locally (powders, ointments, or drops), or as a buccal or nasal spray.

Compositions suitable for parenteral injection may comprise physiologically acceptable sterile aqueous or non-aqueous solutions, dispersions, suspensions or emulsions, and sterile powders for reconstitution into sterile injectable solutions or dispersions. Examples of suitable aqueous and non-aqueous carriers, diluents, solvents, or vehicles include water, ethanol, polyols (propyleneglycol, polyethyleneglycol, glycerol, and the like), suitable mixtures thereof, vegetable oils (such as olive oil), and injectable organic esters such as ethyl oleate. Proper fluidity can be maintained, for example, by the use of a coating such as lecithin, by the maintenance of the required particle size in the case of dispersions and by the use of surfactants.

These compositions may also contain adjuvants such as preserving, wetting, emulsifying, and dispensing agents. Prevention of the action of microorganisms can be ensured by various antibacterial and antifungal agents, for example, parabens, chlorobutanol, phenol, sorbic acid, and the like. It may also be desirable to include isotonic agents, for example sugars, sodium chloride, and the like. Prolonged absorption of the injectable pharmaceutical form can be brought about by the use of agents delaying absorption, for example, aluminum monostearate and gelatin.

Solid dosage forms for oral administration include capsules, tablets, pills, powders, and granules. In such solid dosage forms, the active compound is admixed with at least one inert customary excipient (or carrier) such as sodium citrate or dicalcium phosphate or (a) fillers or extenders, as for example, starches, lactose, sucrose, glucose, mannitol and silicic acid, (b) binders, as for example, carboxymethylcellulose, alignates, gelatin, polyvinylpyrrolidone, sucrose and acacia, (c) humectants, as for example, glycerol, (d) disintegrating agents, as for example, agar-agar, calcium carbonate, potato or tapioca starch, alginic acid, certain complex silicates, and sodium carbonate, (e) solution retarders, as for example paraffin, (f) absorption accelerators, as for example, quaternary ammonium compounds, (g) wetting agents, as for example, cetyl alcohol and glycerol monostearate, (h) adsorbents, as for example, kaolin and bentonite, and (i) lubricants, as for example, talc, calcium stearate, magnesium stearate, solid polyethylene glycols, sodium lauryl sulfate, or mixtures thereof. In the case of capsules, tablets, and pills, the dosage forms may also comprise buffering agents.

Solid compositions of a similar type may also be employed as fillers in soft and hard-filled gelatin capsules using such excipients as lactose or milk sugar as well as high molecular weight polyethyleneglycols, and the like.

Solid dosage forms such as tablets, dragees, capsules, pills, and granules can be prepared with coatings and shells, such as enteric coatings and others well-known in the art. They may contain opacifying agents, and can also be of such composition that they release the active compound or compounds in a certain part of the intestinal tract in a delayed manner. Examples of embedding compositions which can be used are polymeric substances and waxes. The active compounds can also be in micro-encapsulated form, if appropriate, with one or more of the above-mentioned excipients.

Liquid dosage forms for oral administration include pharmaceutically acceptable emulsions, solutions, suspensions, syrups, and elixirs. In addition to the active compounds, the liquid dosage forms may contain inert diluents commonly used in the art, such as water or other solvents, solubilizing agents and emulsifiers, as for example, ethyl alcohol, isopropyl alcohol, ethyl carbonate, ethyl acetate, benzyl alcohol, benzyl benzoate, propyleneglycol, 1,3-butyleneglycol, dimethylformamide, oils, in particular, cottonseed oil, groundnut oil, corn germ oil, olive oil, castor oil and sesame oil, glycerol, tetrahydrofurfuryl alcohol, polyethyleneglycols and fatty acid esters of sorbitan or mixtures of these substances, and the like.

Besides such inert diluents, the composition can also include adjuvants such as wetting agents, emulsifying and suspending agents, sweetening, flavoring, and perfuming agents.

Suspensions, in addition to the active compounds, may contain suspending agents, as for example, ethoxylated isostearyl alcohols, polyoxyethylene sorbitol and sorbitan esters, microcrystalline cellulose, aluminum metahydroxide, bentonite, agar-agar and tragacanth, or mixtures of these substances, and the like.

Compositions for rectal administrations are preferably suppositories which can be prepared by mixing the compounds of the present invention with suitable non-irritating excipients or carriers such as cocoa butter, polyethyleneglycol or a suppository wax, which are solid at ordinary temperatures but liquid at body temperature and therefore, melt in the rectum or vaginal cavity and release the active component.

Dosage forms for topical administration of a compound of this invention include ointments, powders, sprays, and inhalants. The active component is admixed under sterile conditions with a physiologically acceptable carrier and any preservatives, buffers, or propellants as may be required. Ophthalmic formulations, eye ointments, powders, and solutions are also contemplated as being within the scope of this invention.

The compounds of the present invention can typically be administered to a patient at dosage levels in the range of about 0.1 to about 1,000 mg per day. For a normal human adult having a body weight of about 70 kilograms, a dosage in the range of about 0.01 to about 100 mg per kilogram of body weight per day is preferable. The specific dosage used, however, can vary. For example, the dosage can depended on a numbers of factors including the requirements of the patient, the severity of the condition being treated, and the pharmacological activity of the compound being used. The determination of optimum dosages for a particular patient is well-known to those skilled in the art. The term "patient" includes humans and animals.

The term "pharmaceutically acceptable salts, esters, amides, and prodrugs" as used herein refers to those carboxylate salts, amino acid addition salts, esters, amides, and prodrugs of the compounds of the present invention which are, within the scope of sound medical judgment, suitable for use in contact with the tissues of patients without undue toxicity, irritation, allergic response, and the like, commensurate with a reasonable benefit/risk ratio, and effective for their intended use, as well as the zwitterionic forms, where possible, of the compounds of the invention. The term "salts" refers to the relatively non-toxic, inorganic and organic acid addition salts of compounds of the present invention. These salts can be prepared in situ during the final isolation and purification of the compounds or by separately reacting the purified compound in its free base form with a suitable organic or inorganic acid and isolating the salt thus formed. Representative salts include the hydrobromide, hydrochloride, sulfate, bisulfate, nitrate, acetate, oxalate, valerate, oleate, palmitate, stearate, laurate, borate, benzoate, lactate, phosphate, tosylate, citrate, maleate, fumarate, succinate, tartrate, naphthylate mesylate, glucoheptonate, lactiobionate and laurylsulphonate salts, and the like. These may include cations based on the alkali and alkaline earth metals, such as sodium, lithium, potassium, calcium, magnesium and the like, as well as nontoxic ammonium, quaternary ammonium, and amine cations including, but not limited to ammonium, tetramethylammonium, tetraethylammonium, methylamine, dimethylamine, trimethylamine, triethylamine, ethylamine and the like. See, for example, Berge S. M. et al., "Pharmaceutical Salts," *J. Pharm. Sci.*, 1977;66:1–19 which is incorporated herein by reference.

Examples of pharmaceutically acceptable, non-toxic esters of the compounds of this invention include $C_1$–$C_6$ alkyl esters wherein the alkyl group is a straight or branched chain. Acceptable esters also include $C_5$–$C_7$ cycloalkyl esters as well as arylalkyl esters such as, but not limited to, benzyl. $C_1$–$C_4$ alkyl esters are preferred. Esters of the compounds of the present invention may be prepared according to conventional methods.

Examples of pharmaceutically acceptable, non-toxic amides of the compounds of this invention include amides derived from ammonia, primary $C_1$–$C_6$ alkyl amines and secondary $C_1$–$C_6$ dialkyl amines wherein the alkyl groups are straight or branched chain. In the case of secondary amines, the amine may also be in the form of a 5- or 6-membered heterocycle containing one nitrogen atom. Amides derived from ammonia, $C_1$–$C_3$ alkyl primary amines and $C_1$–$C_2$ dialkyl secondary amines are preferred. Amides of the compounds of the invention may be prepared according to conventional methods.

The term "prodrug" refers to compounds that are rapidly transformed in vivo to yield the parent compound of the above formulae, for example, by hydrolysis in blood. A thorough discussion is provided in T. Higuchi and V. Stella, "Pro-drugs as Novel Delivery Systems," Vol. 14 of the A.C.S. Symposium Series, and in *Bioreversible Carriers in Drug Design*, ed. Edward B. Roche, American Pharmaceutical Association and Pergamon Press, 1987, both of which are incorporated herein by reference.

In addition, the compounds of the present invention can exist in unsolvated as well as solvated forms with pharmaceutically acceptable solvents such as water, ethanol, and the like. In general, the solvated forms are considered equivalent to the unsolvated forms for the purposes of the present invention.

The compounds of the present invention can exist in different stereoisometric forms by virtue of the presence of asymmetric centers in the compounds. It is contemplated that all stereoisometric forms of the compounds as well as mixtures thereof, including racemic mixtures, form part of this invention.

In addition, the compounds of the present invention can be made using standard organic chemistry, such as through organic synthesis or using combinatorial chemistry. In addition, the compounds of the present invention can be made through metabolism. It is intended that the invention encompass the compounds made in any manner.

The compounds of the present invention are administered to a patient in need of matrix metalloproteinase inhibition. In general, patients in need of matrix metalloproteinase inhibition are those patients having a disease or condition in which a matrix metalloproteinase plays a role. Examples of such diseases include, but are not limited to, multiple sclerosis, atherosclerotic plaque rupture, restenosis, aortic aneurysm, heart failure, periodontal disease, corneal ulceration, burns, decubital ulcers, chronic ulcers or wounds, cancer metastasis, tumor angiogenesis, osteoporosis, rheumatoid or osteoarthritis, renal disease, left ventricular dilatation, or other autoimmune or inflammatory diseases dependent upon tissue invasion by leukocytes.

A "therapeutically effective amount" is an amount of a compound of Formula I that when administered to a patient having a disease that can be treated with a compound of Formula I ameliorates a symptom of the disease. A therapeutically effective amount of a compound of Formula I is readily determined by one skilled in the art by administering a compound of Formula I to a patient and observing the results.

The following examples illustrate particular embodiments of the invention and are not intended, nor should they be construed, to limit the scope of the specification and claims in any manner. Those skilled in the art will appreciate that modifications and variations of the following can be made without violating the spirit or scope of the specification and claims.

The compounds of the present invention can be obtained using the general synthetic procedure outlined in Scheme 1. The requisite sulfonyl chlorides (1) are readily synthesis by those skilled in the art by direct chlorosulfonation of the parent ring system, or chemical conversion of a substituent on the ring into the sulfonyl chloride (such as the conversion of an amine to a sulfonyl chloride [Meerwein, et al; *Chem. Ber.*, 1957;90:841, which is hereby incorporated by reference]). The sulfonyl chloride (1) is then condensed with an amino acid compound (2) employing a base catalyst such as triethylamine or N-methylmorpholine in a solvent such as dichloromethane or tetrahydrofuran at ambient temperature. If the amino acid compound (2) is protected as a carboxylic ester, it can be easily hydrolyzed to the corresponding carboxylic acid (3) of the present invention. The acid (3) may also be converted to the hydroxamic acid (4) of the present invention by coupling (using standard methods such as an acid halide, a mixed anhydride, or a carbodiimide) with hydroxyl amine (or a suitably O-protected analog which must then be deprotected to give the hydroxamic acid (4)).

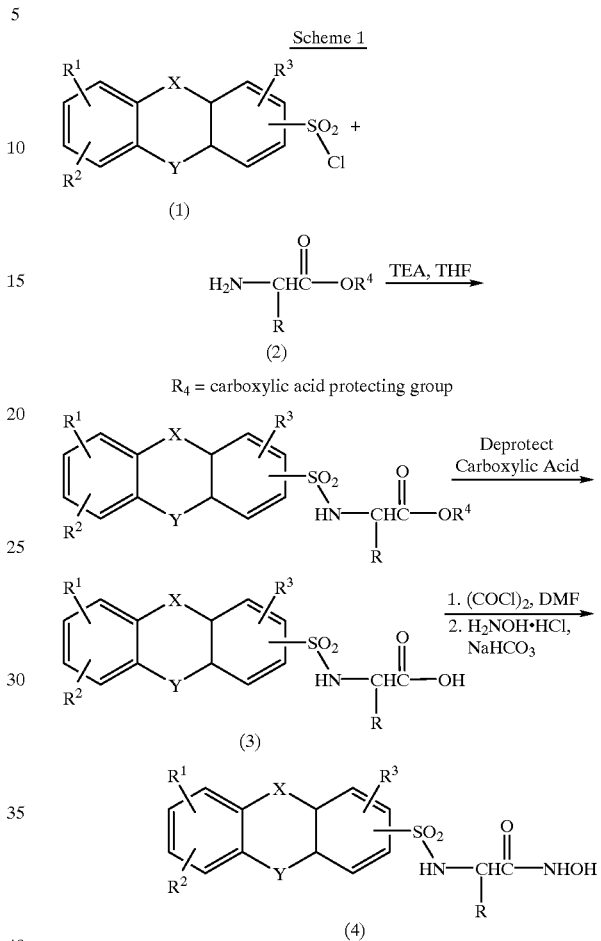

EXAMPLE 1

(S)-3-Methyl-2-((thianthren-2-ylsulfonyl)amino) butanoic acid

Step (a) Thianthrene-2-sulfonyl chloride

To a stirred solution of thianthrene (6.0 g, 27.7 mmol) in 160 mL of dichloromethane at 0° C. was added dropwise, 2.03 mL (30.5 mmol) of chlorosulfonic acid. The resulting deep purple mixture was stirred for 4 hours and then hexanes were added, and the reaction was filtered to give thianthrene-2-sulfonic acid. This acid (3.18 g, 10.7 mmol) was mixed with 7.36 g (35.3 mmol) of phosphorous pentachloride, and the neat solids were heated to a melt at 110° C. for 2 hours. The resulting mixture was quenched with ice and extracted with dichloromethane. The organic phase was dried over magnesium sulfate and concentrated to give the title compound as a green oil which was used without further purification.

Step (b) (S)-3-Methyl-2-((thianthren-2-ylsulfonyl)amino) butanoic acid

The crude thianthrene-2-sulfonyl chloride (1.19 g, 3.77 mmol) was mixed with 0.79 g (3.77 mmol) of (L)-valine-t-butyl ester and triethyl amine (1.58 mL, 11.3 mmol) in 50 mL of dichloromethane. After 2 hours, the reaction was partitioned between 1 M HCl and dichloromethane. The organic phase was washed with saturated sodium carbonate solution, dried over magnesium sulfate, and concentrated to give an oily green solid. This compound (0.46 g, 1.0 mmol) was stirred in 5 mL of trifluoroacetic acid for 1 hour and then concentrated in vacuo. The residue was triturated with diethyl ether to give 0.26 g of the title compound as a fluffy white solid.

$^1$H NMR (DMSO-d$_6$): δ 12.65 (s, 1H), 8.19 (d, 1H), 7.88 (s, 1H), 7.75–7.59 (m, 4H), 7.41–7.39 (m, 2H), 3.57 (m, 1H), 1.98–1.93 (m, 1H), 0.85–0.79 (dd, 6H) ppm.

MS m/z 396 (m+1)

EXAMPLE 2

(S)-2-(Phenoxathiine-2-sulfonylamino)-4-phenyl-butyric acid

Step (a) Phenoxathiine-2-sulfonyl chloride

When in the procedure of Example 1, Step (a), thianthrene is replaced with phenoxathiin, phenoxathiine-2-sulfonyl chloride is obtained as a yellow solid which is used without further purification.

Step (b) (S)-2-(Phenoxathiine-2-sulfonylamino)-4-phenyl-butyric acid

The phenoxathiine-2-sulfonyl chloride (0.75 g, 2.52 mmol) was mixed with (L)-homo-phenylalanine (0.448 g, 2.52 mmol) and triethylamine (1.2 mL, 7.56 mmol) in 50 mL of water and 50 mL of tetrahydrofuran. The resulting mixture was stirred for 2 hours and then concentrated in vacuo. The residue was partitioned between 1 M HCl and ethyl acetate. The organic phase was dried over magnesium sulfate, and concentrated to give an oily solid. Trituration with diethyl ether gave (S)-2-(phenoxathiine-2-sulfonylamino)-4-phenyl-butyric acid as an off-white powder; mp 149–154° C.

MS m/z 442.1 (m+1)

EXAMPLE 3

(S)-4-Phenyl-2-(9H-xanthene-2-sulfonylamino)-butyric acid

Step (a) 9H-xanthene-2-sulfonyl chloride

When in the procedure of Example 1, Step (a), thianthrene is replaced with xanthene, 9H-xanthene-2-sulfonyl chloride is obtained as a pale pink solid which is used without further purification.

Step (b) (S)-4-Phenyl-2-(9H-xanthene-2-sulfonylamino)-butyric acid

When in the procedure of Example 2, Step (b), phenoxathiine-2-sulfonyl chloride is replaced with 9H-xanthene-2-sulfonyl chloride, (S)-4-phenyl-2-(9H-xanthene-2-sulfonylamino)-butyric acid is obtained as a white solid;

mp 138–142° C.

MS m/z 424.2 (m+1)

EXAMPLE 4

(S)-3-Methyl-2-(phenoxathiine-2-sulfonylamino)-butyric acid

When in the procedure of Example 1, Step (b), thianthrene-2-sulfonyl chloride is replaced by phenoxathiine-2-sulfonyl chloride, (S)-3-methyl-2-(phenoxathiine-2-sulfonylamino)-butyric acid is obtained as an off-white solid;

mp 171–175° C.

MS m/z 396 (m+1)

EXAMPLE 5

(S)-3-Hydroxy-2-phenoxathiine-2-sulfonylamino)-propionic acid

A solution of phenoxathiine-2-sulfonyl chloride (1 mL of a 0.2 M) in tetrahydrofuran was mixed with 1 mL of a 0.2 M solution of O-tert-butyl-L-serine, tert-butyl ester hydrochloride in water and 120 mg of a morpholino-resin (prepared according to Booth R. J. and Hodges J. C., *J. Am. Chem. Soc.*, 1997;119(21):4882–4886) in an 8 mL vial. This was shaken for 20 hours and then 70 mg of a poly-amine resin and 70 mg of an isocyanato resin (also both prepared according to Booth and Hodges above, 1997) was added, and the reaction was again shaken for 20 hours. The reaction was filtered, and the filtrate was evaporated. The resulting residue was dissolved in 1 mL of dichloromethane, and 1 mL of trifluoroacetic acid was added. This was shaken for 4 hours and then evaporated to dryness. The product was analyzed by LC (80% water/0.1% formic acid: 20% acetronitrile/0.1% formic acid—gradient to 2:98 over 7 minutes on a 150 mm C18 column, 1 mL/min). R$_f$=5.98 min.

MS m/z 366 (m+1)

EXAMPLE 6

(S)-3-Hydroxy-2-(9H-xanthene-2-sulfonylamino)-propionic acid

When in the procedure of Example 5, phenoxathiine-2-sulfonyl chloride is replaced by 9H-xanthene-2-sulfonyl chloride, (S)-3-hydroxy-2-(9H-xanthene-2-sulfonylamino)-propionic acid is obtained. Rf=5.82 min.

MS m/z 348 (m+1)

EXAMPLE 7

(S)-2-(10,10-Dioxo-10H-10λ$^6$-phenoxathiine-2-sulfonylamino)-4-phenyl-butyric acid (S)-2-(Phenoxathiine-2-sulfonylamino)-4-phenyl-butyric acid (0.5 g, 1.13 mmol) was dissolved in 30 mL of glacial acetic acid, and 5 mL of 30% hydrogen peroxide was added. The resulting mixture was heated to reflux for 1 hour. The reaction was cooled to room temperature and concentrated in vacuo to half the original volume. The residue was partitioned between water and ethyl acetate. The ethyl acetate layer was washed with aqueous sodium bisulfite, dried over magnesium sulfate and concentrated in vacuo to give 0.21 g of (S)-2-(10,10-Dioxo-10H-10λ$^6$-phenoxathiine-2-sulfonylamino)-4-phenyl-butyric acid as an off-white solid; mp 170–174° C.

MS m/z 474 (m+1)

EXAMPLE 8

(R)-3-Methyl-2-(phenoxathiine-2-sulfonylamino)-butyric acid

When in the procedure of Example 1, Step (b), thianthrene-2-sulfonyl chloride is replaced by phenoxathiine-2-sulfonyl chloride and (L)-valine-t-butyl ester is replaced with (D)-valine-t-butyl ester, (S)-3-methyl-2-(phenoxathiine-2-sulfonylamino)-butyric acid is obtained as an off-white solid; mp 171–175° C.

MS m/z 379.9 (m+1)

EXAMPLE 9

(S)-2-(Phenoxathiine-2-sulfonylamino)-propionic acid

When in the procedure of Example 1, Step (b), thianthrene-2-sulfonyl chloride is replaced by phenoxathiine-2-sulfonyl chloride and (L)-valine-t-butyl ester is replaced with (L)-alanine-t-butyl ester, (S)-2-

(phenoxathiine-2-sulfonylamino)-propionic acid is obtained as a white solid; mp 75–85° C.

MS m/z 352 (m+1)

EXAMPLE 10

(S)-4-Methanesulfinyl-2-(phenoxathiine-2-sulfonylamino)-butyric acid

When in the procedure of Example 1, Step (b), thianthrene-2-sulfonyl chloride is replaced by phenoxathiine-2-sulfonyl chloride and (L)-valine-t-butyl ester is replaced with (L)-methionine-t-butyl ester, (S)-4-methanesulfinyl-2-(phenoxathiine-2-sulfonylamino)-butyric acid is obtained as a white solid;

mp 160–170° C.

MS m/z 428 (m+1)

EXAMPLE 11

(S)-4-Methyl-2-(phenoxathiine-2-sulfonylamino)-pentanoic acid

When in the procedure of Example 1, Step (b), thianthrene-2-sulfonyl chloride is replaced by phenoxathiine-2-sulfonyl chloride and (L)-valine-t-butyl ester is replaced with (L)-leucine-t-butyl ester, (S)-4-methyl-2-(phenoxathiine-2-sulfonylamino)-pentanoic acid is obtained; mp 120–130° C.

MS m/z 394 (m+1)

EXAMPLE 12

(S)-2-(Phenoxathiine-2-sulfonylamino)-3-phenyl-propionic acid

When in the procedure of Example 1, Step (b), thianthrene-2-sulfonyl chloride is replaced by phenoxathiine-2-sulfonyl chloride and (L)-valine-t-butyl ester is replaced with (L)-phenylalanine-t-butyl ester, (S)-2-(phenoxanthiine-2-sulfonylamino)-3-phenyl-propionic acid is obtained; mp 120–130° C.

MS m/z 428 (m+1)

EXAMPLE 13

(R)-2-(Phenoxathiine-2-sulfonylamino)-3-tritylsulfanyl-propionic acid

When in the procedure of Example 2, Step (b), (L)-homophenylalanine is replaced with (L)-S-trityl cysteine, (R)-2-(phenoxathiine-2-sulfonylamino)-3-tritylsulfanyl-propionic acid is obtained.

$^1$H-NMR (DMSO-d$_6$) δ 7.31–7.07 (m, 23H), 3.39–3.33 (m, 1H), 2.78 (bd, 1H), 2.23 (bd, 1H) ppm.

EXAMPLE 14

(S)-3-(4-Hydroxy-phenyl)-2-(phenoxathiine-2-sulfonylamino)-propionic acid

When in the procedure of Example 1, Step (b), thianthrene-2-sulfonyl chloride is replaced by phenoxathiine-2-sulfonyl chloride and (L)-valine-t-butyl ester is replaced with (L)-O-t-butyltyrosine-t-butyl ester, (S)-3-(4-hydroxy-phenyl)-2-(phenoxathiine-2-sulfonylamino)-propionic acid is obtained;

mp 180–190° C.

MS m/z 444 (m+1)

EXAMPLE 15

(S)-3-(1H-Indol-3-yl)-2-(phenoxathiine-2-sulfonylamino)-propionic acid

When in the procedure of Example 1, Step (b), thianthrene-2-sulfonyl chloride is replaced by phenoxathiine-2-sulfonyl chloride and (L)-valine-t-butyl ester is replaced with (L)-tryptophan-t-butyl ester, (S)-3-(1H-indol-3-yl)-2-(phenoxathiine-2-sulfonylamino)-propionic acid is obtained; mp 120–130° C.

MS m/z 467 (m+1)

EXAMPLE 16

(S)-2-(Phenoxathiine-2-sulfonylamino)-succinamic acid

When in the procedure of Example 1, Step (b), thianthrene-2-sulfonyl chloride is replaced by phenoxathiine-2-sulfonyl chloride and (L)-valine-t-butyl ester is replaced with (L)-asparagine-t-butyl ester, (S)-2-(phenoxathiine-2-sulfonylamino)-succinamic acid is obtained; mp 165–175° C.

MS m/z 394.9 (m+1)

EXAMPLE 17

(S)-(Phenoxathiine-2-sulfonylamino)-phenyl-acetic acid

When in the procedure of Example 1, Step (b), thianthrene-2-sulfonyl chloride is replaced by phenoxathiine-2-sulfonyl chloride and (L)-valine-t-butyl ester is replaced with (L)-phenylglycine-t-butyl ester, (S)-2-(phenoxathiine-2-sulfonylamino)-phenyl acid is obtained; mp 175–185° C.

MS m/z 414 (m+1)

Biological Assays

Inhibition Studies

Experiments were carried out which demonstrate the efficacy of the compounds of the invention as potent inhibitors of stromelysin-1 and gelatinase A. Experiments were carried out with the catalytic domains; namely, stromelysin-1 (SCD), recombinant gelatinase A (GCD). IC$_{50}$ values were determined using a thiopeptolide substrate, Ac-Pro-Leu-Gly-thioester-Leu-Leu-Gly-OEt (Ye Q. Z., Johnson L. L., Hupe D. J., and Baragi V., "Purification and Characterization of the Human Stromelysin Catalytic Domain Expressed in *Escherichia coli*," *Biochemistry*, 1992;31:11231–11235). MMP-1, MMP-7, and MMP-13 activity was assayed in a method similar to MMP-2 and MMP-3 (SCD and GCD). MMP-1 can be obtained from Washington University School of Medicine, St. Louis, Mo. MMP-7 can be obtained in accordance with the known procedure set forth by Ye Q. Z., Johnson L. L., and Baragi V., "Gene Syntheses and Expression in *E. coli* for PUMP, a Human Matrix Metalloproteinase," *Biochem. and Biophys. Res. Comm.*, 1992;186:143–149. MMP13 can be obtained in accordance with the known procedure set forth by Freije J. M. P. et al., "Molecular Cloning and Expression of Collegenase-3, a Novel Human Matrix Metalloproteinase Produced by Breast Carcinomas," *J. Bio. Chem.*, 1994;269:16766–16773.

Thiopeptolide Assay

Hydrolysis of the thiopeptolide substrate Ac-Pro-Leu-Gly-thioester-Leu-Leu-Gly-OEt (Bachem) is used as the primary screen to determine IC$_{50}$ values for MMP inhibitors.

A 100 μL reaction contains 1 mM 5,5'-dithiobis(2-nitrobenzoic acid) (DTNB), 100 μM substrate, 0.1% BRIJ® 35, PROTEIN GRADE®, Detergent, 10% solution, Sigma, St. Louis, Mo. [polyoxyethyleneglycol dodecyl ether; polyoxyethylene (23) lauryl ether], enzyme, and inhibitor in the appropriate reaction buffer. Activated full-length enzymes are assayed at 5 nM, Stromelysin Catalytic Domain (SCD) at 10 nM, and Gelatinase A Catalytic Domain (GaCD) at 1 nM. Inhibitors are screened from 100 μM to 1 nM. Full-length enzymes (MMP-1 and MMP-7) are assayed in 50 mM HEPES, 10 mM $CaCl_2$, pH 7.0; SCD in 50 mM MES, 10 mM $CaCl_2$, pH 6.0; and GaCD in 50 mM MOPS, 10 mM $CaCl_2$, 10 μM $ZnCl_2$, pH 7.0. The change in absorbance at 405 nM is monitored on a ThermoMax microplate reader at room temperature continuously for 20 minutes.

Ac is acetyl;

Pro is proline;

Leu is leucine;

Gly is glycine;

Et is ethyl;

HEPES is 4-(2-hydroxymethyl)-piperazine-1-ethane sulfonic acid;

MES is 2-morpholinoethane sulfonic acid monohydrate; and

MOPS is 3-morpholtriopropane sulfonic acid.

The results are depicted in Table 1.

TABLE 1

| | $IC_{50}$ (μM) | | | | | | |
|---|---|---|---|---|---|---|---|
| Example | MMP-1 | MMP-2CD | MMP-3CD | MMP-7 | MMP-9 | MMP-13CD | MMP-14CD |
| 1 | >100 | 15.4 | 6.9 | 27.6 | >100 | >100 | 40 |
| 2 | >100 | 0.033 | 0.054 | 7.9 | 16.63 | 1.39 | 0.092 |
| 3 | >100 | 0.2 | 0.068 | 3.2 | >100 | 0.5 | 1 |
| 4 | 39 | 0.0335 | 0.053 | 6.7 | 19 | 4.1 | 0.28 |
| 5 | >100 | 0.069 | 0.18 | 23 | 82 | 1.8 | 0.39 |
| 6 | >100 | 0.65 | 0.44 | 34 | >100 | 4.3 | 4.1 |
| 7 | >100 | 2.3 | 3.75 | 24 | >100 | 73 | 3.7 |
| 8 | 6.25 | 0.027 | 0.0155 | 19 | 12 | 0.27 | 0.155 |
| 9 | 76 | 0.033 | 0.295 | 19 | 23 | 5.25 | 0.19 |
| 10 | 72 | 0.0585 | 0.165 | 9.15 | 38 | 4.1 | 0.285 |
| 11 | 55 | 0.0235 | 0.0625 | 8.7 | 18 | 3.9 | 0.3 |
| 12 | >100 | 0.17 | 0.35 | 91 | >100 | 8.7 | 0.5 |
| 13 | >100 | 3.2 | 4.65 | 66 | >100 | 36 | 7.4 |
| 14 | 87 | 0.09 | 0.12 | 17 | 18 | 2.3 | 0.2 |
| 15 | >100 | 0.91 | 0.86 | 54 | >100 | 16 | 3.8 |
| 16 | >100 | 0.1133 | 0.41 | 14 | 53 | 4.4 | 1.55 |
| 17 | >100 | 0.15 | 2 | >100 | >100 | 12 | 0.94 |

What is claimed is:

1. A compound of Formula I:

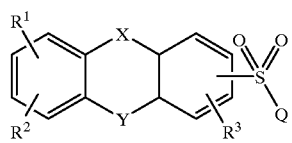

I and pharmaceutically acceptable salts, esters, amides, and prodrugs thereof, wherein X and Y are independently O, $S(O)_n$, $CH_2$, C=O, NH, or $NC_1-C_6$ alkyl, provided that X and Y are not both

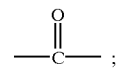

n is 0, 1, or 2;

each $R^1$, $R^2$, and $R^3$ are independently halogen, hydrogen, $-NO_2$, $-NH_2$, $-NH(C_1-C_6 alkyl)$, $-N(C_1-C_6 alkyl)_2$, $-CN$, $-CF_3$, $-C_1-C_6$ alkyl, $-C_1-C_6$ alkoxy, $-CO_2H$, or $-CO_2C_1-C_6$ alkyl;

Q is an amino acid residue wherein the amino acid is selected from:

D-alanine, D-valine, D-leucine, D-isoleucine, D-phenylalanine, D-proline, D-serine, D-threonine, D-tyrosine, D-asparagine, D-glutamine, D-lysine, D-arginine, D-tryptophan, D-histidine, D-cysteine, D-methionine, D-aspartic acid, D-glutamic acid, D-homophenylalanine, L-alanine, L-valine, L-leucine, L-isoleucine, L-phenylalanine, L-proline, L-serine, L-threonine, L-tyrosine, L-asparagine, L-glutamine, L-lysine, L-arginine, L-tryptophan, L-histidine, L-cysteine, L-methionine, L-aspartic acid, L-glutamic acid, or L-homophenylalanine.

2. A compound in accordance with claim 1 wherein Q is D-alanine, D-valine, D-leucine, D-isoleucine, D-phenylalanine, D-proline, D-serine, D-threonine, D-tyrosine, D-asparagine, D-glutamine, D-lysine, D-arginine, D-tryptophan, D-histidine, D-cysteine, D-methionine, D-aspartic acid, D-glutamic acid, or D-homophenylalanine.

3. A compound in accordance with claim 1 wherein Q is L-alanine, L-valine, L-leucine, L-isoleucine, L-phenylalanine, L-proline, L-serine, L-threonine, L-tyrosine, L-asparagine, L-glutamine, L-lysine, L-arginine, L-tryptophan, L-histidine, L-cysteine, L-methionine, L-aspartic acid, L-glutamic acid, or L-homophenylalanine.

4. A compound in accordance with claim 1 wherein the compound is:

(2S)-3-Methyl-2-((thianthren-2-ylsulfonyl)amino) butanoic acid;

(2S)-4-Phenyl-2-((phenoxathiin-3-ylsulfonyl)amino)butanoic acid;
(S)-4-Phenyl-2-(9H-xanthene-2-sulfonylamino)-butyric acid;
(S)-3-Methyl-2-(phenoxathiine-2-sulfonylamino)-butyric acid;
(S)-3-Hydroxy-2-(phenoxathiine-2-sulfonylamino)-propionic acid;
(S)-3-Hydroxy-2-(9H-xanthene-2-sulfonylamino)-propionic acid;
(S)-2-(10,10-Dioxo-10H-10$\lambda^6$-phenoxathiine-2-sulfonylamino)-4-phenyl-butyric acid;
(R)-3-Methyl-2-(phenoxathiine-2-sulfonylamino)-butyric acid;
(S)-2-(Phenoxathiine-2-sulfonylamino)-propionic acid;
(S)-4-Methanesulfinyl-2-(phenoxathiine-2-sulfonylamino)-butyric acid;
(S)-4-Methyl-2-(phenoxathiine-2-sulfonylamino)-pentanoic acid;
(S)-2-(Phenoxathiine-2-sulfonylamino)-3-phenyl-propionic acid;
(R)-2-(Phenoxathiine-2-sulfonylamino)-3-tritylsulfanyl-propionic acid;
(S)-3-(4-Hydroxy-phenyl)-2-(phenoxathiine-2-sulfonylamino)-propionic acid;
(S)-3-(1H-Indol-3-yl)-2-(phenoxathiine-2-sulfonylamino)-propionic acid;
(S)-2-(Phenoxathiine-2-sulfonylamino)-succinamic acid; and
(S)-(Phenoxathiine-2-sulfonylamino)-phenyl-acetic acid.

5. A compound in accordance with claim 1 wherein the compound is:
(R)-3-Hydroxy-2-(phenoxathiine-2-sulfonylamino)-propionic acid;
(R)-3-Hydroxy-2-(9H-xanthene-2-sulfonylamino)-propionic acid;
(S)-3-Hydroxy-2-(9H-xanthene-2-sulfonylamino)-propionic acid;
(S)-2-(10,10-Dioxo-10H-10$\lambda^6$-phenoxathiine-2-sulfonylamino)-4-phenyl-butyric acid;
(R)-2-(10,10-Dioxo-10H-10$\lambda^6$-phenoxathiine-2-sulfonylamino)-4-phenyl-butyric acid;
(R)-2-(Phenoxathiine-2-sulfonylamino)-propionic acid;
(S)-2-(9H-Xanthene-2-sulfonylamino)-propionic acid;
(R)-2-(9H-Xanthene-2-sulfonylamino)-propionic acid;
(S)-2-(Phenoxathiine-3-sulfonylamino)-succinic acid; and
(R)-2-(Phenoxathiine-3-sulfonylamino)-succinic acid.

6. A compound in accordance with claim 1 wherein the compound is:
(R)-2-(9H-Xanthene-3-sulfonylamino)-succinic acid;
(S)-2-(9H-Xanthene-3-sulfonylamino)-succinic acid;
(R)-2-(10,10-Dioxo-10H-10$\lambda^6$-phenoxathiine-3-sulfonylamino)-succinic acid;
(S)-2-(10,10-Dioxo-10H-10$\lambda^6$-phenoxathiine-3-sulfonylamino)-succinic acid;
(S)-2-(10,10-Dioxo-10H-10$\lambda^6$-phenoxathiine-2-sulfonylamino)-propionic acid;
(R)-2-(10,10-Dioxo-10H-10$\lambda^6$-phenoxathiine-2-sulfonylamino)-propionic acid;
(R)-2-(10,10-Dioxo-10H-10$\lambda^6$-phenoxathiine-2-sulfonylamino)-3-hydroxy-propionic acid;
(S)-2-(10,10-Dioxo-10H-10$\lambda^6$-phenoxathiine-2-sulfonylamino)-3-hydroxy-propionic acid;
(S)-2-(10,10-Dioxo-10H-10$\lambda^6$-phenoxathiine-2-sulfonylamino)-3-methyl-butyric acid; and
(R)-2-(10,10-Dioxo-10H-10$\lambda^6$-phenoxathiine-2-sulfonylamino)-3-methyl-butyric acid.

7. A compound in accordance with claim 1 wherein the compound is:
(S)-3-Benzyloxy-2-(phenoxathiine-2-sulfonylamino)-propionic acid;
(R)-3-Benzyloxy-2-(phenoxathiine-2-sulfonylamino)-propionic acid;
(S)-3-Benzyloxy-2-(10,10-dioxo-10H-10$\lambda^6$-phenoxathiine-2-sulfonylamino)-propionic acid;
(R)-3-Benzyloxy-2-(10,10-dioxo-10H-10$\lambda^6$-phenoxathiine-2-sulfonylamino)-propionic acid;
(S)-3-Benzyloxy-2-(9H-xanthene-2-sulfonylamino)-propionic-acid; and
(R)-3-Benzyloxy-2-(9H-xanthene-2-sulfonylamino)-propionic acid.

8. A compound in accordance with claim 1 wherein the group

is located at the 2- or 3-position.

9. A method of inhibiting a matrix metalloproteinase in a patient in need of matrix metalloproteinase inhibition, the method comprising administering to the patient a therapeutically effective amount of a compound of claim 1.

10. A method of treating multiple sclerosis, the method comprising administering to a patient having multiple sclerosis a therapeutically effective amount of a compound of claim 1.

11. A method of treating atherosclerotic plaque rupture, the method comprising administering to a patient having an atherosclerotic plaque at risk for rupture a therapeutically effective amount of a compound of claim 1.

12. A method of treating or preventing restenosis, the method comprising administering to a patient having restenosis or at risk of having restenosis a therapeutically effective amount of a compound of claim 1.

13. A method of treating aortic aneurysm, the method comprising administering to a patient having aortic aneurysm a therapeutically effective amount of a compound of claim 1.

14. A method of treating heart failure, the method comprising administering to a patient having heart failure a therapeutically effective amount of a compound of claim 1.

15. A method of treating periodontal disease, the method comprising administering to a patient having periodontal disease a therapeutically effective amount of a compound of claim 1.

16. A method of treating corneal ulceration, the method comprising administering to a patient having corneal ulceration a therapeutically effective amount of a compound of claim 1.

17. A method of treating burns, the method comprising administering to a patient having burns a therapeutically effective amount of a compound of claim 1.

18. A method of treating decubital ulcers, the method comprising administering to a patient having decubital ulcers a therapeutically effective amount of a compound of claim 1.

19. A method of treating chronic ulcers or wounds, the method comprising administering to a patient having chronic ulcers or wounds a therapeutically effective amount of a compound of claim 1.

20. A method of treating cancer metastasis, the method comprising administering to a patient having cancer a therapeutically effective amount of a compound of claim 1.

21. A method of treating tumor angiogenesis, the method comprising administering to a patient having tumor angiogenesis a therapeutically effective amount of a compound of claim 1.

22. A method of treating arthritis, the method comprising administering to a patient having arthritis a therapeutically effective amount of a compound of claim 1.

23. The method of claim 22 wherein the arthritis is rheumatoid arthritis.

24. The method of claim 22 wherein the arthritis is osteoarthritis.

25. A method of treating osteoporosis, the method comprising administering to a patient having osteoporosis a therapeutically effective amount of a compound of claim 1.

26. A method of treating renal disease, the method comprising administering to a patient having renal disease a therapeutically effective amount of a compound of claim 1.

27. A method of treating left ventricular dilatation, the method comprising administering to a patient having left ventricular dilatation a therapeutically effective amount of a compound of claim 1.

28. A method of treating autoimmune or inflammatory diseases dependent upon tissue invasion by leukocytes, the method comprising administering to a patient having autoimmune or inflammatory diseases dependent upon tissue invasion by leukocytes a therapeutically effective amount of a compound of claim 1.

* * * * *